United States Patent
Spakevicius

(10) Patent No.: US 10,933,009 B2
(45) Date of Patent: Mar. 2, 2021

(54) FORMULATIONS AND METHODS FOR TREATING DERMATOLOGICAL DISORDERS AND DISEASES

(71) Applicant: VAPOGENIX, INC., Houston, TX (US)

(72) Inventor: Danguole Spakevicius, Houston, TX (US)

(73) Assignee: Vapogenix, Inc., Houston, TX (US)

(*) Notice: Subject to any disclaimer, the term of this patent is extended or adjusted under 35 U.S.C. 154(b) by 41 days.

(21) Appl. No.: 15/979,056

(22) Filed: May 14, 2018

(65) Prior Publication Data

US 2018/0256477 A1    Sep. 13, 2018

Related U.S. Application Data

(63) Continuation of application No. 14/129,017, filed as application No. PCT/US2012/043493 on Jun. 21, 2012, now Pat. No. 9,968,540.

(60) Provisional application No. 61/500,909, filed on Jun. 24, 2011.

(51) Int. Cl.
| | |
|---|---|
| *A61K 8/69* | (2006.01) |
| *A61K 8/14* | (2006.01) |
| *A61K 9/00* | (2006.01) |
| *A61K 47/22* | (2006.01) |
| *A61K 9/107* | (2006.01) |
| *A61K 9/127* | (2006.01) |
| *A61K 31/075* | (2006.01) |
| *A61Q 19/00* | (2006.01) |

(52) U.S. Cl.
CPC ............ *A61K 8/69* (2013.01); *A61K 8/14* (2013.01); *A61K 9/0014* (2013.01); *A61K 9/107* (2013.01); *A61K 9/1075* (2013.01); *A61K 9/127* (2013.01); *A61K 31/075* (2013.01); *A61K 47/22* (2013.01); *A61Q 19/004* (2013.01); *A61Q 19/007* (2013.01)

(58) Field of Classification Search
CPC .... A61K 9/0014; A61K 9/107; A61K 9/1075; A61Q 19/007
See application file for complete search history.

(56) References Cited

U.S. PATENT DOCUMENTS

| | | |
|---|---|---|
| 5,114,714 A | 5/1992 | Young et al. |
| 5,114,715 A | 5/1992 | Young et al. |
| 5,183,585 A | 2/1993 | Koyama et al. |
| 5,227,165 A | 7/1993 | Domb et al. |
| 5,230,778 A | 7/1993 | Gavlin et al. |
| 5,283,372 A | 2/1994 | Rozov et al. |
| 5,336,429 A | 8/1994 | Barthelemy et al. |
| 6,080,744 A | 6/2000 | Ayon-Covarrubias |
| 9,968,540 B2 * | 5/2018 | Spakevicius ......... A61K 9/0014 |
| 2005/0238677 A1 | 10/2005 | Mercier et al. |
| 2007/0149624 A1 | 6/2007 | Suzuki et al. |
| 2008/0119820 A1 | 5/2008 | Phan et al. |
| 2010/0047187 A1 | 2/2010 | Hampton |
| 2011/0039944 A1 | 2/2011 | Capelli et al. |
| 2013/0273141 A1 | 10/2013 | Burton et al. |

FOREIGN PATENT DOCUMENTS

| | | |
|---|---|---|
| EP | 0273202 A2 | 7/1988 |
| EP | 2839828 A1 | 2/2015 |
| JP | S60501557 A | 9/1985 |
| JP | 2003520769 U | 7/2003 |
| JP | 2006504740 A | 2/2006 |
| JP | 2011-510092 A | 3/2011 |
| WO | 2005108383 A2 | 11/2005 |
| WO | 2009094460 A2 | 7/2009 |
| WO | 2010129686 A1 | 11/2010 |

OTHER PUBLICATIONS

Schmelz, Martin, "Itch and pain," Neuroscience & Biobehavioral Reviews, vol. 34, No. 2, pp. 171-176 (Year: 2010).*
Merck Manual, 18th Edition, Japanese Version, Nov. 2005, [online], retrieved on Nov. 2, 2016 from the Internet: <URL: http://merckmanual.jp/mmpej/sec21/ch315/ch315h.html>. *English version*.
Haynes, et al., "Ultra-long-duration Local Anesthesia Produced by Injection of Lecithin-coated Methoxyflurane Microdroplets," Anesthesiology, vol. 63, No. 5, 1985, pp. 490-499.
Haynes, et al., "Long Duration Local Anesthesia with Lecithin-coated Microdroplets of Methoxyflurane: Studies with Human Skin," Regional Anesthesia, vol. 16, 1991, pp. 173-180.

* cited by examiner

*Primary Examiner* — Dennis J Parad
(74) *Attorney, Agent, or Firm* — Saul Ewing Arnstein & Lehr LLP; Kathryn Doyle; Domingos J. Silva

(57) ABSTRACT

The present invention provides compositions and methods for treating a dermatological disorder or disease.

3 Claims, 1 Drawing Sheet

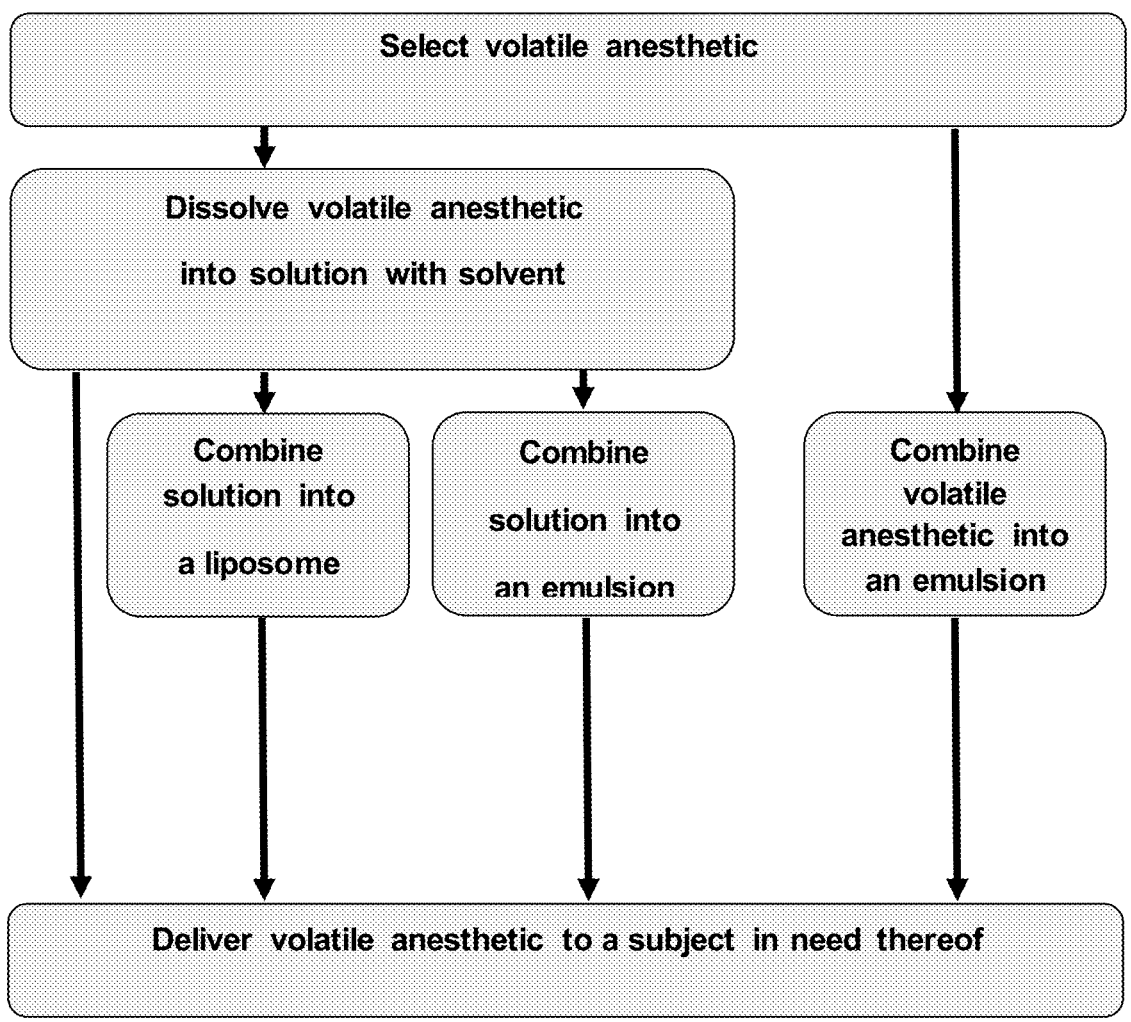

FORMULATIONS AND METHODS FOR TREATING DERMATOLOGICAL DISORDERS AND DISEASES

CROSS-REFERENCE TO RELATED APPLICATION

The present application is a continuation of, and claims priority to, U.S. patent application Ser. No. 14/129,017, filed Feb. 26, 2014, now issued as U.S. Pat. No. 9,968,540, which is the U.S. national phase application filed under 35 U.S.C. § 371 claiming priority to International Patent Application No. PCT/US2012/043493, filed Jun. 21, 2012, which claims priority pursuant to 35 U.S.C. § 119(e) to U.S. Provisional Application No. 61/500,909, filed Jun. 24, 2011, all of which applications are hereby incorporated by reference herein in their entireties.

BACKGROUND OF THE INVENTION

Skin is the soft outer covering of animals. In mammals, the skin is the largest organ of the integumentary system and is made up of multiple layers of ectodermal tissue. Because it interfaces with the environment, the skin has the important function of protecting the underlying muscles, bones, ligaments and internal organs from outside contact or injury. The skin further plays a key role in protecting the body against pathogens and excessive water loss. Among the skin's other functions are thermal insulation and regulation, gas absorption, sensation (the skin contains nerve endings that respond to heat and cold, touch, pressure, vibration, and tissue injury), and synthesis of vitamin D folates.

The skin may be affected by disorders or diseases that are diverse in terms of cause, presentation and/or treatment. Among the most common skin disorders or diseases are dermatitis/eczema, psoriasis and itching.

Dermatitis is generally caused by an allergic reaction to specific allergens. The term "dermatitis" is often used interchangeably with the term "eczema," which is also called dermatitis eczema or eczematous dermatitis. Dermatitis comprises conditions such as: contact dermatitis (caused by an allergen or an irritating substance); atopic dermatitis; dermatitis herpetiformis (which appears as a result of celiac disease); seborrheic dermatitis; nummular dermatitis (which tends to appear more frequently in middle-aged people); stasis dermatitis (an inflammation on the lower legs which is caused by buildups of blood and fluid and more likely 24550027.2 to occur in people with varicose); and perioral dermatitis (which is similar to rosacea and often observed in women between 20 and 60 years old).

Dermatitis symptoms range from skin rashes to bumpy rashes, including blisters. Although every type of dermatitis has different symptoms, there are presentations that are common for all of them, including redness of the skin, swelling, itching, skin lesions and sometimes oozing and scarring. Also, the area of the skin on which the symptoms appear may be different with each type of dermatitis. The symptoms of contact dermatitis usually appear at the site where the allergen got into contact with the skin. Although the symptoms of atopic dermatitis vary from person to person, the most common symptoms are dry, itchy, red skin. Typically affected skin areas include the folds of the arms, the back of the knees, wrists, face and hands. Less commonly there may be cracks behind the ears, and various other rashes on any part of the body. http://en.wikipedia.org/wiki/Dermatitis—cite_note-5 Itching is the primary symptoms of this condition.

Treatment of dermatitis is made accordingly with the particular cause of the disease. Application of corticosteroidal creams or wet compresses and avoidance of allergens and irritants are part of most treatment plans. For some types of dermatitis, non-steroidal medications and occasional use of over-the-counter antihistamines may help relieve signs and symptoms.

Psoriasis is a chronic immune-mediated skin disease that appears when the immune system sends out faulty signals that speed up the growth cycle of skin cells. Psoriasis is not contagious and is commonly seen as red and white hues of scaly patches (plaques) appearing on the top first layer of the epidermis. Some patients, though, have no dermatological symptoms. Plaques frequently occur on the skin of the elbows and knees, but can affect any area, including the scalp, palms of hands and soles of feet, and genitals. In contrast to eczema, psoriasis is more likely to be found on the outer side of the joint.

Psoriasis is a chronic recurring condition that varies in severity from minor localized patches to complete body coverage. Fingernails and toenails are frequently affected (psoriatic nail dystrophy) and can be seen as an isolated symptom. Psoriasis can also cause inflammation of the joints, which is known as psoriatic arthritis. Between 10% and 40% of all people with psoriasis have psoriatic arthritis.

The cause of psoriasis is not fully understood, but it is believed to have a genetic component and local psoriatic changes can be triggered by an injury to the skin. Various environmental factors have been suggested as aggravating to psoriasis, including stress and withdrawal of systemic corticosteroid. There are treatments available (such as topical agents, phototherapy, and systemic agents, such as methotrexate, cyclosporine and retinoids) but psoriasis treatment is challenging because of the chronic recurrent nature of the disease.

Itching is a sensation that causes the desire or reflex to scratch. The behavioral response patterns of pain and itching are intrinsically different: pain creates a withdrawal reflex, while itch leads to a scratch reflex. Unmyelinated nerve fibers for itch and pain both originate in the skin; however, information for them is conveyed centrally in two distinct systems that both use the same peripheral nerve bundle and spinothalamic tract. Itching may be triggered by infections and infestations, environmental and allergic triggers, dermatological disorders (such as dry skin, psoriasis, eczema, sunburn, topical fungal infections (such as but not limited to athlete's foot, ringworm, and onychomycosis), hidradenitis suppurativa, scab healing, scar growth, development or emergence of moles, pimples and ingrown hairs from below the epidermis, punctate palmoplantar keratoderma and dandruff), medical disorders (malignancy or internal cancer such as lymphoma and Hodgkin's disease), jaundice and cholestasis, polycythemia, thyroid illness, hyperparathyroidism, uraemia, diabetes mellitus, iron deficiency anemia, menopause or changes in hormonal balances associated with aging), medication (morphine and other opiates, chloroquine) and conditions related to pregnancy (intrahepatic cholestasis of pregnancy, pruritic urticarial papules and plaques of pregnancy (PUPPP) and gestational pemphigoid).

Itching is often treated with over-the-counter and prescription anti-itch drugs, such as antihistamines (such as diphenhydramine), corticosteroids (such as hydrocortisone topical cream), counterirritants (such as mint oil, menthol, or camphor), and crotamiton. Phototherapy is helpful for severe itching, especially if caused by renal failure.

Volatile anesthetics have been used safely for decades as general anesthetics. Recently, volatile anesthetics have been shown to be useful in the treatment of pain by administration routes rather than inhalation. For example, International Application Publication No. WO 2009/094460 discloses compositions and methods useful for reducing pain in a subject in need thereof by delivering a volatile anesthetic in a solution or an emulsion to the subject. Besides producing analgesia, volatile anesthetics affect other receptors and have been shown to have anti-inflammatory and muscle relaxing properties. For example, International Application Publication No. WO 2010/129686 discloses compositions and methods useful for treating inflammation or a wound in a subject in need of such wound treatment or inflammation treatment by delivering a volatile anesthetic to the wound or the inflammation site. Volatile anesthetics have been further shown to reduce cytokine production and release in both in vivo and in vitro inflammation model, and downregulate lipopolysaccharide (LPS)-induced production of pro-inflammatory cytokines. Additionally, volatile anesthetics have been shown to inhibit neutrophil function and decrease time to resolution of inflammation. However, volatile anesthetics have not been so far successfully used in the treatment of skin disorders or diseases.

There is a need in the art for improved formulations that may be used in the treatment of dermatological disorders or diseases. There is also a need in the art for improved methods for treating dermatological disorders or diseases. The current invention fulfills these needs.

BRIEF SUMMARY OF THE INVENTION

The invention includes a pharmaceutically acceptable composition for treating a dermatological disorder or disease. The composition comprises a pharmaceutically acceptable excipient and at least one component selected from the group consisting of: (a) a metered amount of a volatile anesthetic dissolved in a solution in an amount effective to treat the dermatological disorder or disease, wherein the solution further comprises at least one extractive solvent in an amount effective to reduce volatility of the volatile anesthetic, wherein the solution is a component of an emulsion; (b) a metered amount of a liposome suspension comprising a volatile anesthetic in an amount effective to treat the dermatological disorder or disease; (c) a metered amount of a volatile anesthetic dissolved in a solution in an amount effective to treat the dermatological disorder or disease, wherein the solution further comprises at least one extractive solvent in an amount effective to reduce volatility of the volatile anesthetic, wherein the composition further comprises a solubilizing agent; (d) a metered amount of a micro-droplet suspension, wherein the micro-droplet suspension comprises a sphere of a volatile anesthetic in an amount effective to treat the dermatological disorder or disease, wherein the sphere is surrounded by a stabilizing layer of a phospholipid; and any combinations thereof.

In one embodiment, the at least one extractive solvent is selected from the group consisting of dimethyl sulfoxide (DMSO), N-methyl-2-pyrrolidone (NMP), dimethylformamide, dimethylacetamide, dimethylisosorbide, ethanol, propanol, PEG-400, PEG-300, diethylene glycol monoethyl ether, isopropanol and any combinations thereof. In another embodiment, the composition is formulated for an administration route selected from the group consisting of topical, transdermal, mucosal, rectal, vaginal and any combinations thereof. In yet another embodiment, the volatile anesthetic is selected from the group consisting of isoflurane, halothane, enflurane, sevoflurane, desflurane, methoxyflurane, xenon and any mixtures thereof. In yet another embodiment, the dermatological disorder or disease is selected from the group consisting of eczema, dermatitis, psoriasis, itching, urticaria, allodynia, dry skin, sunburn, topical bacterial infections, topical fungal infections, hidradenitis suppurativa, scab healing, scar growth, development or emergence of moles, pimples, ingrown hair, punctate palmoplantar keratoderma, dandruff and any combinations thereof.

The invention also includes a method of treating a dermatological disorder or disease in a subject in need thereof. The method comprises administering to the subject a pharmaceutically acceptable composition, wherein the composition comprises a pharmaceutically acceptable excipient and at least one component selected from the group consisting of: (a) a metered amount of a volatile anesthetic dissolved in a solution in an amount effective to treat the dermatological disorder or disease, wherein the solution further comprises at least one extractive solvent in an amount effective to reduce volatility of the volatile anesthetic, wherein the solution is a component of an emulsion; (b) a metered amount of a liposome suspension comprising a volatile anesthetic in an amount effective to treat the dermatological disorder or disease; (c) a metered amount of a volatile anesthetic dissolved in a solution in an amount effective to treat the dermatological disorder or disease, wherein the solution further comprises at least one extractive solvent in an amount effective to reduce volatility of the volatile anesthetic, wherein the composition further comprises a solubilizing agent; (d) a metered amount of a micro-droplet suspension, wherein the micro-droplet suspension comprises a sphere of a volatile anesthetic in an amount effective to treat the dermatological disorder or disease, wherein the sphere is surrounded by a stabilizing layer of a phospholipid; and any combinations thereof. In one embodiment, the at least one extractive solvent is selected from the group consisting of dimethyl sulfoxide (DMSO), N-methyl-2-pyrrolidone (NMP), dimethylformamide, dimethylacetamide, dimethylisosorbide, ethanol, propanol, PEG-400, PEG-300, diethylene glycol monoethyl ether, isopropanol and any combinations thereof. In another embodiment, the administering is performed by a route selected from the group consisting of topical, transdermal, mucosal, rectal, vaginal and any combinations thereof. In yet another embodiment, the volatile anesthetic is selected from the group consisting of isoflurane, halothane, enflurane, sevoflurane, desflurane, methoxyflurane, xenon and any mixtures thereof. In yet another embodiment, the dermatological disorder or disease is selected from the group consisting of eczema, dermatitis, psoriasis, itching, urticaria, allodynia, dry skin, sunburn, topical bacterial infections, topical fungal infections, hidradenitis suppurativa, scab healing, scar growth, development or emergence of moles, pimples, ingrown hair, punctate palmoplantar keratoderma, dandruff and any combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 illustrates a flowchart representing general methods for making compositions for the delivery of a formulated volatile anesthetic to the affected area of a subject.

DETAILED DESCRIPTION OF THE INVENTION

The present invention relates to the unexpected discovery that the compositions and methods of the invention are useful to treat, ameliorate or prevent a dermatological disorder or disease, such as but not limited to eczema, psoriasis and itching. In one embodiment, the itching is associated with pain. In another embodiment, the itching is not associated with pain.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "or," as used herein, means "and/or" unless explicitly indicated to refer to alternatives only or the alternatives are mutually exclusive, although the disclosure supports a definition that refers to only alternatives and "and/or."

The terms "inhibiting," "reducing," "preventing," "diminishing," and variations of these terms, as used herein include any measurable decrease, including complete or substantially complete inhibition.

The term "effective," as that term is used in the specification and/or claims, means adequate to accomplish a desired, expected, or intended result.

The phrase "extractive solvent," as used herein, refers to a solvent that may interact with a volatile anesthetic in solution to reduce the volatility of the volatile anesthetic without chemically reacting to the volatile anesthetic, and/or enhances permeability of volatile anesthetic into the tissue of interest, favoring either achievement or enhancement of an intended pharmacological outcome. Extractive solvents also comprise compounds that do not necessarily extract, including vehicles and functional components that may affect properties such as, but not limited to, permeability or penetration.

As used herein, the term "enhanced permeability" refers to increase in (a) amount of volatile anesthetic delivered to the tissue of interest and/or (b) rate of delivery (i.e., rapid delivery) to the tissue of interest and/or (c) residence time of volatile anesthetic in the tissue of interest. Increase in residence time refers to a delay in elimination of volatile anesthetic from tissue of interest.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "dermatological disorder or disease" refers to a condition associated with the skin. Examples of these disorders or diseases include, but are not limited to, eczema, dermatitis, psoriasis, itching, urticaria, dry skin, sunburn, topical bacterial infections (such as but not limited to impetigo, folliculitis, furunculosis, carbunculosis, ecthyma, erysipelas, cellulitis and necrotizing fasciitis), topical fungal infections (such as but not limited to athlete's foot, toe fungus, tinea corporis, tinea cruris, tinea faciei, tinea manuum, tinea pedis, any other form of ringworm, and onychomycosis), hidradenitis suppurativa, scab healing, scar growth, development or emergence of moles, pimples, ingrown hair, punctate palmoplantar keratoderma and dandruff. Itching may be associated with one or more of these dermatological disorders or diseases, as well as allodynia, malignancy or internal cancer such as lymphoma and Hodgkin's disease, jaundice, cholestasis, polycythemia, thyroid illness, hyperparathyroidism, uraemia, diabetes mellitus, iron deficiency anemia, menopause or changes in hormonal balances associated with aging, use of morphine and other opiates, use of chloroquine, and conditions related to pregnancy (intrahepatic cholestasis of pregnancy, pruritic urticarial papules and plaques of pregnancy (PUPPP) and gestational pemphigoid).

As used herein, the term "allodynia" refers to a form of pain due to a stimulus which does not normally provoke pain. Allodynia may be either thermal or mechanical in origin, and often occurs after injury to a site. Allodynia is distinct from hyperalgesia, an extreme reaction to a stimulus that is normally painful. There are different kinds or types of allodynia: mechanical allodynia (also known as tactile allodynia), which includes atatic mechanical allodynia (pain in response to light touch/pressure) and dynamic mechanical allodynia (pain in response to brushing); and thermal (hot or cold) allodynia (pain from normally mild skin temperatures in the affected area).

The term "topical," as used herein, refers to the administration of the compositions of the invention to the skin and underlying tissues, as well as to administration to the mucosa and underlying tissues.

The term "treat" or "treatment," as used herein, refers to the alleviation (i.e., "diminution") and/or the elimination of a sign/symptom or a source of a sign/symptom. By way of several non-limiting examples, a dermatological disorder or disease may be treated by alleviating or eliminating a sign/symptom of the dermatological disorder or disease. By way of a further example, a dermatological disorder or disease may be treated by aiding (e.g., accelerating) the healing process of the dermatological disorder or disease.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

DESCRIPTION

The invention includes a pharmaceutically acceptable composition comprising a metered amount of a volatile anesthetic dissolved in an aqueous solution in an amount effective to treat, ameliorate or prevent a dermatological disorder or disease, wherein the solution further comprises at least one extractive solvent in an amount effective to reduce volatility of the volatile anesthetic, wherein the solution is a component of an emulsion, wherein the composition further comprises a pharmaceutically acceptable excipient.

The invention further includes a pharmaceutically acceptable composition comprising a metered amount of a volatile anesthetic emulsion.

The invention also includes a pharmaceutically acceptable composition comprising a metered amount of a volatile anesthetic dissolved in a solution in an amount effective to treat, ameliorate or prevent a dermatological disorder or disease, wherein the solution further comprises at least one extractive solvent in an amount effective to reduce volatility of the volatile anesthetic, wherein the composition further comprises a solubilizing agent, wherein the composition further comprises a pharmaceutically acceptable excipient.

The invention further includes a pharmaceutically acceptable composition comprising a metered amount of a micro-droplet suspension, wherein the micro-droplet suspension comprises a sphere of a volatile anesthetic surrounded by a stabilizing layer of a phospholipid, wherein the composition further comprises a pharmaceutically acceptable excipient.

The invention also included a pharmaceutically acceptable composition comprising a metered amount of a volatile anesthetic dissolved in an aqueous solution in an amount effective treat, ameliorate or prevent a dermatological disorder or disease, wherein the solution is a component of an emulsion, wherein the composition further comprises a pharmaceutically acceptable excipient.

In one embodiment, the at least one extractive solvent is selected from the group consisting of dimethyl sulfoxide (DMSO), N-methyl-2-pyrrolidone (NMP), dimethylformamide, dimethylacetamide, dimethylisosorbide, ethanol, propanol, PEG-400, PEG-300, diethylene glycol monoethyl ether, isopropanol, and mixtures thereof. Preferably, the at least one extractive solvent comprises from about 0.1% to about 75% of the solution.

In one embodiment, the solution is sterile. This may be achieved by ensuring that all starting materials are sterile and maintaining them under sterile conditions prior to administration. This may also be achieved by incorporation of an antimicrobial filter as has been done with various types of infusions (see, for example, U.S. Pat. No. 5,695,490).

In one embodiment, the composition is formulated for an administration by a route selected from the group consisting of topical, transdermal, mucosal, rectal, and vaginal.

In one embodiment, the volatile anesthetic is selected from the group consisting of isoflurane, halothane, enflurane, sevoflurane, desflurane, methoxyflurane, xenon and mixtures thereof. In another embodiment, the volatile anesthetic is isoflurane. Many of these agents are racemic mixtures. In some embodiments, the racemic mixtures are used. In other embodiments, only the d-isomer or the l-isomer of an agent is used (for examples, see U.S. Pat. Nos. 5,114,715; 5,114,714 and 5,283,372). In yet another embodiment, the solution may comprise from about 1% to about 99% v/v, from about 5% to about 70% v/v, or about 50% v/v, or about 25% v/v, or about 10% v/v volatile anesthetic in solution.

In one embodiment, the emulsion comprises a lipid. In another embodiment, the lipid comprises an agent selected from the group consisting of soybean oil, olive oil, peanut oil, castor oil, corn oil and sesame oil. The emulsion may further comprise an emulsifier.

In one embodiment, the volatile anesthetic is in the form of a suspension, a cream, a paste, an oil, a lotion, a gel, a foam, a hydrogel, an ointment, a liposome, an emulsion, a liquid crystal emulsion, or a nano-emulsion.

In one embodiment, the composition further comprises an antibiotic.

In one embodiment, the solution comprises at least one constituent selected from the group consisting of water and a saline solution.

In one embodiment, the diameter of the microdroplet ranges from about 200 Angstroms up to about 10,000 Angstroms. In another embodiment, the micro-droplets are produced by sonication, homogenization, microfluidization or other processes involving high shear, wherein the ratio of the volume of the volatile anesthetic to the weight of the phospholipid layer is at least 1.0 ml/g and the composition contains at least 3% w/v of the volatile anesthetic. The invention further includes a method of treating, ameliorating or preventing a dermatological disorder or disease in a subject in need thereof, wherein the method comprises administering to the subject a volatile anesthetic dissolved in a solution in an amount effective to treat, ameliorate or prevent the dermatological disorder or disease, wherein the solution further comprises at least one extractive solvent in an amount effective to reduce volatility of the volatile anesthetic, wherein the solution is a component of an emulsion, wherein the route of administration is selected from the group consisting of topical, transdermal, mucosal, rectal, and vaginal.

The invention also includes a method of treating, ameliorating or preventing a dermatological disorder or disease in a subject in need thereof, wherein the method comprises administering to the wound of the subject a volatile anesthetic dissolved in a solution in an amount effective to treat, ameliorate or prevent the dermatological disorder or disease, wherein the solution further comprises at least one extractive solvent in an amount effective to reduce volatility of the volatile anesthetic, wherein the composition further comprises a solubilizing agent, wherein the administration route is selected from the group consisting of topical, transdermal, mucosal, rectal, and vaginal.

The invention further includes a method of treating, ameliorating or preventing a dermatological disorder or disease in a subject in need thereof, wherein the method comprises administering to the subject a volatile anesthetic dissolved in a solution in an amount effective to treat, ameliorate or prevent the dermatological disorder or disease, wherein the solution is a component of an emulsion, wherein the administration route is selected from the group consisting of topical, transdermal, mucosal, rectal, and vaginal.

The invention also includes a method of treating, ameliorating or preventing a dermatological disorder or disease in a subject in need thereof, wherein the method comprises administering to the subject a liposome suspension comprising a volatile anesthetic in an amount effective to treat, ameliorate or prevent the dermatological disorder or disease, wherein the administration route is selected from the group consisting of topical, transdermal, mucosal, rectal, and vaginal.

The invention further includes a method of treating, ameliorating or preventing a dermatological disorder or disease in a subject in need thereof, the method comprising administering to the subject a micro-droplet suspension comprising a sphere of a volatile anesthetic surrounded by a stabilizing layer of a phospholipid in an amount effective to treat, ameliorate or prevent the dermatological disorder or disease, wherein the administration route is selected from the group consisting of topical, transdermal, mucosal, rectal, and vaginal.

In one embodiment, the dermatological disorder or disease is selected from the group consisting of eczema, dermatitis, psoriasis, itching, urticaria, allodynia, dry skin, sunburn, topical bacterial infections (such as but not limited to impetigo, folliculitis, furunculosis, carbunculosis, ecthyma, erysipelas, cellulitis and necrotizing fasciitis), topical fungal infections (such as but not limited to athlete's foot, tinea faciei, any other form of ringworm, and onychomycosis), hidradenitis suppurativa, scab healing, scar growth, development or emergence of moles, pimples, ingrown hair, punctate palmoplantar keratoderma and dandruff. In another embodiment, itching may be associated with a condition selected from the group consisting of eczema, dermatitis, psoriasis, urticaria, dry skin, sunburn, topical bacterial infections, topical fungal infections (such as but not limited to athlete's foot, tinea faciei, any other form of ringworm, and onychomycosis), hidradenitis suppurativa, scab healing, scar growth, development or emergence of moles, pimples, ingrown hair, punctate palmoplantar keratoderma, dandruff, malignancy or internal cancer such as lymphoma and Hodgkin's disease, jaundice, cholestasis, polycythemia, thyroid illness, hyperparathyroidism, uraemia, diabetes mellitus, iron deficiency anemia, menopause or changes in hormonal balances associated with aging, use of morphine and other opiates, use of chloroquine, and conditions related to pregnancy (intrahepatic cholestasis of pregnancy, pruritic urticarial papules and plaques of pregnancy (PUPPP) and gestational pemphigoid).

In a non-limiting aspect, the presence of an extractive solvent in the composition of the invention comprising the volatile anesthetic may provide substantial advantages, including improving the physical characteristics, pharmacological properties, and/or the ease of use of the composition. The extractive solvent may interact with the volatile anesthetic (in a non-limiting example, isoflurane) in a non-azeotropic fashion to effectively reduce vaporization or evaporation of the volatile anesthetic. This effect of reducing volatility may be referred to as volatility attenuating effect (VAE). In this way, the shelf-life, durability, and/or ease of use of a volatile anesthetic composition may be improved.

In a non-limiting aspect, the pharmacokinetics of the volatile anesthetic may be altered by the presence of an extractive solvent. For example, without wishing to be bound by any theory, the extractive solvent may function in certain embodiments as a reservoir for the volatile anesthetic such that the amount of volatile anesthetic retained and/or the duration of retention is enhanced as compared to the application of pure non-formulated volatile anesthetic. Hence an extractive solvent renders delivery of the volatile anesthetic to a particular site of action more effective. Similarly, in one embodiment where the volatile anesthetic composition contains an extractive solvent, the extractive solvent may facilitate absorption, in terms of rate and/or extent, of the volatile anesthetic into the site of action.

Additionally, presence of an extractive solvent may have additive or synergistic contributions to the volatility attenuation effect (VAE) rendered by the vehicle. In this aspect, the formulation may facilitate retention of the volatile anesthetic, which otherwise would be prone to rapidly escape from the site of action due to its highly volatile nature, even at room temperature.

In a non-limiting aspect, when the formulation is a component of an emulsion or of a liposome, the emulsion or the liposome may function as a reservoir for the volatile anesthetic to retain the volatile anesthetic in a particular region more effectively and/or help deliver the volatile anesthetic to site(s) of action. In yet another non-limiting aspect, the delivery of the volatile anesthetic may be tailored as a sustained release. This may eliminate or reduce the need for repeated dosing, and/or allow the achievement of the desired steady-state drug levels. Reduced volatility of the volatile anesthetic in composition may also improve the ease of handling the volatile anesthetic compositions. This may facilitate manufacturing and packaging the compositions of the invention. This may also avoid the possibility of inhalation of the volatile anesthetic by the patient, health care provider or packaging facility worker. Further, the reduced vaporization of a volatile anesthetic in solution due to the presence of an extractive solvent may also reduce any potential concerns of a possible risk of fire and/or exposure at the medical facility.

In a non-limiting embodiment, when administered topically to an affected area, it is desirable to achieve a clinically effective concentration, which in some, but not necessarily all, cases may range, for example, from about 5 µg/mL to about 2,000,000 µg/mL of active agent in a formulation. In another non-limiting embodiment, in topical administration it is desirable to achieve a clinically effective concentration, which in some, but not necessarily all, cases may range, for example, from about 2 µL to about 50 µL of solution per centimeter square of area of application.

The invention further includes a sealed container comprising a volatile anesthetic solution of the present invention. The interior of the container may be sterile. The container may be, for example, a syringe, a plastic bag, a collapsible plastic bag, a glass bottle, a glass ampoule or a plastic bottle. The container may be itself a skin dressing or part of a skin dressing. In another aspect of present invention, a container that offers many advantages, such as, for example, ease of application, unit dose configuration, and excellent container-closure compatibility profile, is contemplated. This container may be such that the volatile anesthetic solution is contained in a crushable sealed ampoule. The ampoule is in turn enclosed in protective covering on which pressure is applied to crush the ampoule, which then releases volatile anesthetic solution for percolation through a flint-type tip which capped the ampoule in protective covering. When such packaging configuration is employed, care is taken to leave as little as possible or ideally no headspace in ampoule for the volatile anesthetic to escape and cause a change in solution composition over a period of shelf life.

Extractive Solvents

The volatile anesthetic compositions of the present invention may contain a solvent, such as an extractive solvent, in combination with a volatile anesthetic. The phrase "extractive solvent," as used herein, refers to a solvent that may interact with a volatile anesthetic in the compositions of the invention to reduce the volatility of the volatile anesthetic without chemically reacting with the anesthetic. This phrase also includes compounds that do not necessarily extract, including vehicles and functional components, which may affect properties such as, but not limited to, permeability or penetration.

Certain extractive solvents interact in a non-azeotropic fashion with a volatile anesthetic. Nonetheless, the term "extractive solvent," as used herein, may include certain compounds, or mixtures thereof, which interact with a volatile anesthetic to form an azeotropic or pseudoazeotropic solution as long as the vapor pressure or evaporation of the volatile anesthetic from the solution is reduced. Extractive solvents are also expected to attenuate volatility of volatile anesthetics such that the time required for a given amount of anesthetic to escape from a given surface at a given temperature is increased, resulting in appreciable increase in time of contact of volatile anesthetic with the site of application before complete evaporation of unabsorbed portion, as compared with the application of pure volatile anesthetic under similar conditions. In another embodiment, formulations of current invention may contain an extractive solvent such that this extractive solvent enhances permeability of volatile anesthetic into the tissue of interest thus favoring either achievement of or enhancement of an intended pharmacological outcome. By way of example, but not limitation, the tissue of interest described above may be skin or any other tissue involved or believed to be involved, directly or indirectly, in the intended pharmacological outcome. Enhanced permeability, as it applies to current invention, refers to increase in: (a) amount of volatile anesthetic delivered to the tissue of interest, and/or (b) rate of delivery (i.e., rapid delivery) to the tissue of interest, and/or (c) residence time of volatile anesthetic in the tissue of interest. Increase in residence time refers to a delay in elimination of volatile anesthetic from tissue of interest.

As described below by chemical class as well as individual examples, various extractive solvents are envisioned for use with the present invention. The chemical classes contemplated in this invention comprise fatty alcohols, fatty acids, fatty amines, fatty acid esters, polyols, terpenes, esters, ethers, alkoxylated amides, poly propylene glycol ethers, polyethylene glycols, poly propylene glycols and poly propylene glycol ethers. Selected examples of individual ingredients contemplated in current invention comprise of polyethylene glycol 400, polyethylene glycol 300, diethylene glycol monoethyl ether, Labrasol, oleoyl macrogolglycerides (Labrafil M 1944), linoleoyl macrogolglycerides (Labrafil M2125), lauroyl macrogoglycerides (Labrafil M 2130), propylene glycol dicaprylocaprate, propylene glycol monocaprylate (Capryol 90, Capryol PGMC), polypropylene glycol monolaurate (Lauroglycol 90, Lauroglycol FCC), polyglyceryl-3-dioleate, Peceol, isostearyl isostearate, propylene glycol dipelargonate, polyglyceryl-3 dioleate, propylene glycol dipelargonate, octyldodecyl myristate, diethyl sebacate, diisopropyl adipate, ethyl oleate, glyceryl isostearate, isopropyl isostearate, isopropyl myristate, isostearyl alcohol, isostearic acid, oleyl alcohol, eicosapentanenoic acid, docosahexaenoic acid, olive oil, peanut oil, soybean oil, castor oil, corn oil, cottonseed oil, peppermint oil, safflower oil, sesame oil, soybean oil, hydrogenated soybean oil, hydrogenated vegetable oil, medium chain triglycerides coconut oil, palm oil, liquid lanolin, DMSO, NMP, and the like.

The exact concentration of an extractive solvent may be determined empirically and may vary according to the specific volatile anesthetic used. In certain embodiments, the extractive solvent is present in the composition in an amount effective to reduce volatility of the volatile anesthetic in the composition. Particular care should also be taken to select a concentration of an extractive solvent that results in little or no toxicity when administered. It will be understood that, although certain extractive solvents may exhibit properties which might be used in various separation procedures (e.g., extractive distillation), extractive solvents according to embodiments of the present invention are preferably included in pharmacological mixtures or solutions comprising a volatile anesthetic in order to reduce the volatility of, rather than "extract," the volatile anesthetic.

Including an extractive solvent in an anesthetic composition may increase the ease with which one may mix the solution prior to administration. For example, in certain embodiments, mixing prior to administration may be desirable if final formulation is selected to be self-emulsifying drug delivery system (SEDDS). In certain embodiments, sonication of the anesthetic solution prior to administration is not required when an extractive solvent is included in the volatile anesthetic composition. This advantage may be particularly useful in instances (e.g., chronic administration) where the presence of a sonicator could be noisy or distracting, such as an operating room, and the elimination in the noise of a sonicator may also create an improved environment for a conscious patient receiving a volatile anesthetic composition, e.g., chronically or intermittently for pain relief. Eliminating the need for a sonicator, or other similar device, may also be particularly useful for reducing costs associated with administration of a volatile anesthetic composition according to the present invention. The reduction in the bulk associated with the presence of a sonicator may beneficially improve patient mobility. For example, in instances where a patient may receive repeated administrations of an anesthetic composition via a pump for analgesia, the reduced amount of equipment may improve mobility since the patient is not required to additionally move a sonicator. In certain embodiments, sonication of the anesthetic solution prior to administration is required when an extractive solvent is included in the volatile anesthetic composition.

Extractive solvents are known in the art and are typically used in extractive distillation for separating compounds with similar boiling points by retarding the vapor pressure of the principal component, thereby making possible an efficient separation which would not at all occur in the absence of such solvent. For example, U.S. Pat. No. 5,230,778 describes the purification of isoflurane by extractive distillation using extractive solvents such as dimethylformamide. U.S. Pat. No. 5,336,429 describes solvents for cleaning electronic components and for degreasing metals comprising isoflurane and a lower alcohol or an ester, although these compositions are described as azeotropic mixtures with virtually constant boiling points. In contrast, the present invention provides pharmaceutical preparations, for example, for reating, ameliorating or preventing a dermatological disorder or disease.

Certain extractive solvents known in the art, such as acetone as described in U.S. Pat. No. 5,230,778, may be sufficiently toxic to limit their inclusion in pharmaceutical preparations at higher concentrations.

In certain embodiments, an extractive solvent may interact as an azeotropic mixture with an anesthetic and reduce the volatility of the anesthetic. For example, ethanol may interact in an azeotropic fashion with a volatile anesthetic as described in U.S. Pat. No. 5,230,778.

Various concentrations of an extractive solvent may be used with the present invention. For example, a composition of the present invention comprising a volatile anesthetic may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80%, or any range derivable therein, of an extractive solvent.

In certain embodiments, the extractive solvent is polyethylene glycol 400 (PEG 400) or polyethylene glycol 300 (PEG 300). In other embodiments, vehicle is olive oil or peanut oil or liquid lanolin or diethylene glycol monoethyl ether.

In certain embodiments, the extractive solvent is diethylene glycol monoethyl ether. In other embodiments, functional component is ethyl oleate, glyceryl isostearate, isopropyl isostearate, isopropyl myristate, isostearyl alcohol, isostearic acid or oleyl alcohol. In certain embodiments, the extractive solvent is dimethylsulfoxide (DMSO) or N-methyl-2-pyrrolidone (NMP). In other embodiments, an extractive solvent such as dimethylformamide, dimethylacetamide, or dimethylisosorbide may be used. In instances where acetone is used, care should be taken to choose an appropriate dose in order to minimize any possible toxicity.

Other extractive solvents include PEG-400, PEG-300, and diethylene glycol monoethyl ether.

In various embodiments, it is envisioned that a medically acceptable alcohol, such as ethanol, propanol, or isopropanol may be used. In these embodiments, the concentration of the alcohol used is sufficiently dilute in solution such that little or no irritation or neuron death occurs as a result of injection of the solution near a nerve.

A single extractive solvent, or multiple extractive solvents, may be present in an anesthetic composition of the present invention. For example, in certain embodiments, only a single extractive solvent (e.g., DMSO, NMP or PEG 400) is present in a composition comprising a volatile anesthetic. In other embodiments, two, three, four or more extractive solvents may be present in a composition comprising a volatile anesthetic. In certain embodiments, only a single volatile anesthetic (e.g., isoflurane) is present in an anesthetic composition of the present invention; in other embodiments, two, three, four or more volatile anesthetics may be present in an anesthetic composition of the present invention. In certain embodiments, only a single extractive solvent (e.g., diethylene glycol monoethyl ether) is present in an anesthetic composition of the present invention. In other embodiments, two, three, four or more extractive solvents may be present in an anesthetic composition of the present invention.

N-Methyl pyrrolidone:

N-methyl-2-pyrrolidone (NMP) is a solvent that may be included in the volatile anesthetic compositions according to the present invention. NMP is a chemical compound with 5-membered lactam structure. It is a clear to slightly yellow liquid miscible with water and solvents including ethyl acetate, chloroform, benzene and lower alcohols or ketones. NMP is also referred to by the chemical names 1-methyl-2-pyrrolidone or N-methyl-2-pyrrolidinone and m-pyrrole. NMP belongs to the class of dipolar aprotic solvents, which also includes dimethylformamide, dimethylacetamide and dimethyl sulfoxide. Due to its good solvency properties, NMP has been used to dissolve a wide range of chemicals, particularly in the polymers field. It also used as a solvent for surface treatment of textiles, resins and metal coated plastics or as a paint stripper.

NMP has been used in the medical industry to improve the solubility of poorly soluble drugs in certain pharmaceutical formulations. For example, NMP has been used with various drugs in veterinary medicine. Several patents have been issued, claiming improvements in drug solubility by the use of NMP, as well as its applicability in topical and transdermal pharmaceutical products for humans.

The relatively non-toxic properties of NMP make it particularly suitable for use as a solvent with the present invention. NMP has a favorable toxicity profile making it a suitable candidate for use in a variety of topical, transdermal and parenteral dosage forms. NMP is available in GMP grade under the trademark Pharmasolve N-methyl-2-pyrrolidone sold by International Specialty Products (ISP; New Jersey, USA).

Dimethyl Sulfoxide (DMSO):

Dimethyl sulfoxide (DMSO) is used in certain embodiments of the present invention as a solvent. DMSO has the formula $(CH_3)_2SO$. DMSO is a polar aprotic solvent that dissolves both polar and non-polar compounds and is miscible in a wide range of organic solvents as well as water.

DMSO is a relatively non-toxic compound, which makes it particularly suitable for use as a solvent within the present invention. The relative lack of toxicity of DMSO is well established, and the potential use of DMSO for medical purposes was established by Stanley Jacob at the University of Oregon Medical School team, who discovered DMSO could penetrate the skin and other membranes without damaging them and could carry other compounds into a biological system. DMSO has also been used as a cryoprotectant and as an anti-inflammatory agent. Dimethyl sulfoxide dissolves a variety of organic substances, including carbohydrates, polymers, peptides, as well as many inorganic salts and gases.

In various embodiments, it is envisioned that lower concentrations, for example, as low as from about 0.1% to about 10%, of DMSO in a composition comprising a volatile anesthetic may be sufficient to eliminate the need for sonication of the composition prior to administration. Higher concentrations, for example, from about 10% to about 75% or higher, of DMSO in a composition comprising a volatile anesthetic may be sufficient to alter the pharmacokinetics of the volatile anesthetic in such a way to allow for an increased rate and/or extent of volatile anesthetic delivered.

Volatile Anesthetics

In general, the halogenated ether anesthetics or volatile anesthetics suitable for use with the described compositions and methods include agents which, although often liquid at room temperature, are capable of easily being becoming gaseous or are already gaseous at room temperature and may treat dermatological disorders or diseases without significant side effects. It may be desirable, for example, to select a volatile anesthetic that is minimally metabolized by the body or is otherwise inert. In this way, liver and kidney toxicity may be minimized. Similarly, it may be desirable for the volatile anesthetic to have a short half-life, or be fast acting to promote titratability (i.e., the subject may easily adjust the delivery amount for the dermatological disorder or disease he or she is experiencing). An active agent gas that does not produce tolerance (unlike opioids or local volatile anesthetics) or dependence (like opioids) may also be desirable.

Volatile anesthetics useful in the compositions and methods of the invention include halogenated ether compounds, isoflurane, sevoflurane, halothane, enflurane, desflurane, methoxyflurane, and diethyl ethers. In certain embodiments xenon may also be used with the present invention. A single agent or mixtures of agents may be particularly suitable for use with the methods described herein.

In various embodiments, a gaseous volatile anesthetic may be used with the present invention. For example, the gaseous volatile anesthetic may be dissolved in a solution according to the present invention and administered in a regional or local procedure, such as transdermally, topically, mucosally, rectally, orally, or vaginally. Importantly, the gaseous volatile anesthetic is not administrated by inhalation. Gaseous volatile anesthetics other than halogenated anesthetics are contemplated, and examples include xenon, nitrous oxide, cyclopropane, and ether, all of which may be used, in various embodiments, in racemic mixture form, or in d-isomer or l-isomer forms. In various embodiments, other biologically active gases (for example, nitric oxide) may be delivered in a solution to a subject according to the present invention.

More than one volatile anesthetic may be administered at one time, and different volatile anesthetics may be administered at various times throughout a single treatment cycle. For example, two, three, four or more volatile anesthetics may be simultaneously or repeatedly administered to a subject. When compounds are repeatedly administered to a subject, the duration between administration of compounds may be about 1-60 seconds, 1-60 minutes, 1-24 hours, 1-7 days, 1-6 weeks or more, or any range derivable therein. In some instances, it may be desirable to stage the delivery of volatile anesthetics depending on their physical and physiological properties. In certain clinical scenarios, a shorter acting agent may be desirable to treat acute dermatological disorders or diseases, whereas a longer lasting agent may be more suited to chronic dermatological disorders or diseases.

Antibiotics

Antibiotics useful in the compositions and methods of the invention include known antibiotics, as well as those yet to be discovered. Non-limiting examples include Amikacin, Aminoglycoside, Amoxicillin, Ampicillin, Azithromycin, Bacampicillin, Candicidin, Carbenicillin, Cefaclor, Cefadroxil, Cefamandole, Cefazolin, Cefdinir, Cefditoren, Cefepime, Cefonicid, Cefoperazone, Cefotaxime, Cefotetan, Cefoxitin, Cefpodoxime, Cefprozil, Ceftazidime, Ceftibuten, Ceftizoxime, Ceftriaxone, Cefuroxime, Cephalexin, Cephalosporins, Cephapirin, Cephradine, Ciprofloxacin, Clarithromycin, Clindamycin, Clotrimazole, Cloxacillin, Crysticillin, Cuprimyxin, Pentids, Permapen, Pfizerpen, Pfizerpen-AS, Wycillin, Demeclocycline, Dicloxacillin, Dirithromycin, Doxycycline, Enoxacin, Erythromycin, Flucloxacillin, Fluoroquinolone, Gatifloxacin, Gemifloxacin, Gentamicin, Haloprogin, Iodochlorohydroxyquin, Kanamycin, Ketolide, Levofloxacin, Lipopeptides, Lomefloxacin, Macrolides, Metronidazole, Mezlocillin, Minocycline, Moxifloxacin, Nafcillin, Neomycin, Netilmicin, Norfloxacin, Nystatin, Ofloxacin, Oxacillin, Oxytetracycline, Paromomycin, Penicillin G, Penicillin V, Penicillins, Piperacillin, Pivampicillin, Pivmecillinam, Roxithromycin, Sparfloxacin, Streptomycin, Sulfamethizole, Sulfamethoxazole, Sulfisoxazole, Sulfonamides, Telithromycin, Tetracyclines, Ticarcillin, Tobramycin, Tolnaftate, Trimethoprim-Sulfamethoxazole, Trovafloxacin, and Vancomycin.

Emulsions

As would be understood by one skilled in the art, an emulsion consists of a mixture of two or more immiscible liquids (i.e., contains multiple phases) and emulsions are distinct from solutions, which contain one or essentially only one phase. One of the liquids (the dispersed phase) is dispersed in the other (the continuous phase). In one type of emulsion, a continuous liquid phase surrounds droplets of water (for example, a water-in-oil emulsion). In another type of emulsion, oil is dispersed within a continuous water phase (for example, an oil-in-water emulsion). Similarly, emulsification is the process by which emulsions are prepared.

In certain embodiments, a volatile anesthetic of the present invention is a component of an emulsion, such as a water-in-oil or an oil-in-water emulsion, including, but not limited to a lipid emulsion, such as a soybean oil emulsion. For example, a volatile anesthetic composition comprising a volatile anesthetic dissolved in a solution comprising an extractive solvent may also comprise a lipid emulsion or an oil-in-water emulsion. In various embodiments, the emulsion of the invention may contain an aqueous solution comprising a volatile anesthetic dissolved in a solution, which may further comprise an extractive solvent. Inclusion of a water-in-oil or an oil-in-water emulsion, such as, for example, a lipid emulsion, in an volatile anesthetic composition may be used, for example, to favorably affect the stability of the volatile anesthetic composition and/or alter the pharmacokinetics of the anesthetic. For example, lipid compositions, lipid emulsions, water-in-oil emulsions, and/or oil-in-water emulsions may be useful for the transdermal, topical, mucosal, rectal, or vaginal delivery of the volatile anesthetic compositions of the present invention. Certain emulsions of isoflurane have been prepared previously for intravenous (da Silva Telles et al., 2004, Rev. Bras. Anaestesiol Campianas 54(5):2004) or epidural administration (Chai et al., 2008, British J Anesthesia 100:109-115; Chai et al., 2006, Anesthesiology 105:A743), both for inducing anesthesia.

In certain embodiments, the emulsion of the invention comprises a volatile anesthetic and water, and may further comprise an emulsifier. Emulsions of the invention also include, but are not limited to, nanoemulsions, which are emulsions with a mean droplet size less than those of emulsions. Nanoemulsions are sometimes referred to as microemulsions and submicroemulsions. Often, the physical appearance of a nanoemulsion is transparent, rather than the often milky appearance of an emulsion, due to the reduced mean droplet size. Emulsions of the invention also include, but are not limited to, liquid crystal emulsions, such as those disclosed, for example, in U.S. Patent Application Nos. 20070149624 and 20050238677, U.S. Pat. No. 5,183,585 and International Patent Application No. WO 05108383.

In certain embodiments, the emulsion of the invention may have a lipid component. In various embodiments, the lipid component may comprise an amount ranging from about 1% to 99%, from about 5% to about 75%, from about 10% to about 60%, from about 20% to about 50%, or from about 30% to about 40%, v/v of the emulsion. In various embodiments, the lipid component of the emulsion may be soybean oil, long chain triglyceride, castor oil, corn oil, cottonseed oil, olive oil, peanut oil, peppermint oil, safflower oil, sesame oil, soybean oil, hydrogenated soybean oil, hydrogenated vegetable oil, medium chain triglycerides coconut oil, palm see oil and derivatives, medium chain (C8/C10) mono- and diglycerides, d-alpha-tocopherol, soy fatty acids, or combinations thereof. In certain embodiments, the lipid component of the emulsion is soybean oil. Commercially available lipid compositions that may be useful for the production of the volatile anesthetic compositions of the present invention include, but are not limited to, Intralipid®, Liposyn®, and Nutrilipid®.

In other embodiments, the emulsion further comprises an emulsifier. An emulsifier is a substance that stabilizes an emulsion. An emulsifier may also known as an emulgent. An emulsifier may also be a surfactant. In various embodiments, the emulsifier may be egg phospholipid, purified egg phospholipids, Polyoxyl 35 castor oil (Cremophor EL), Polyoxyl 40 hydrogenated castor oil (Cremophor RH 40), Polyoxyl 60 hydrogenated castor oil (Cremophor RH 60), Polysorbate 20, Polysorbate 80, d-alpha-tocopheryl polyethylene glycol 1000 succinate, Solutol HS-15, propylene glycol, or combinations thereof. Various concentrations of an emulsifier may be used with the present invention. For example, a composition of the present invention comprising a volatile anesthetic may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an emulsifier.

In other embodiments, the emulsion of the invention has a perfluorocarbon component. In various embodiments, the perfluorocarbon component may comprise an amount ranging from about 0.1% to 99%, from about 5% to about 75%, from about 10% to about 60%, from about 20% to about 50%, or from about 30% to about 40%, v/v of the emulsion. In various embodiments, perfluorocarbon may provide additional advantages due to its limited toxicity and ability to scavenge a large amount of gas. In one embodiment, the emulsion of the invention comprises a volatile anesthetic, a perfluorocarbon, water and an emulsifier. A perfluorocarbon, specifically perfluoro-n-octane, has been used clinically, in cases of retinal detachment, by its instillation into the eye in place of the aqueous humor (see Chang, 1992, S. Intl. Ophthalmol. Clinic 32:153-163).

Liposomes and Micro-Droplets

In various embodiments, the volatile anesthetics of the present invention may be a component of a liposome suspension. A liposome (for example, multilamellar, unilamellar, and/or multivesicular liposomes) is a microscopic, spherical, fluid-filled structure, with walls comprising one or more layers of phospholipids and molecules similar in physical and/or chemical properties to those that make up mammalian cell membranes. By way of non-limiting examples, liposomes may be formed from a variety of natural membrane components, such as cholesterol, stearylamine, or phosphatidylcholine (see, for example, U.S. Pat. Nos. 5,120,561 and 6,007,838, each of which is incorporated herein by reference in its entirety), or of pure surfactant components like DOPE (dioleoylphosphatidylethanolamine). Liposomes may be formulated to incorporate a wide range of materials as a payload either in the aqueous or in the lipid compartments or in both. Generally, lipophilic active substances dissolve in the bilayer, amphiphilic substances become associated with the phospholipid membrane and hydrophilic substances occur in solution in the enclosed aqueous volume (Artmann et al., 1990, Drug Res. 40 (II) 12:1363-1365; incorporated herein by reference in its entirety).

Liposomes are useful as drug carriers or for topical use (Gehring et al., 1990, Drug Res. 40 (II) 12:1368-1371; incorporated herein by reference in its entirety). Liposomes have been used as carriers for lipophilic drugs like the anti-tumor and the anti-viral derivatives of azidothymidine (AZT) (Kamps, et al., 1996, Biochim. Biophys. Acta. 1278: 183-190). Insulin has also been delivered via liposomes (Muramatsu et al., 1999, Drug Dev. Ind. Pharm. 25:1099-1105). For medical uses as drug carriers, the liposomes may also be injected, and when they are modified with lipids, their surfaces become more hydrophilic and hence their ability to persist may be increased. Polyethylene glycol-modified liposomes have been used as carriers for hydrophilic (water-soluble) anti-cancer drugs like doxorubicin. Liposomal derivatives of mitoxantrone and others are especially effective in treating diseases that affect the phagocytes of the immune system because they tend to accumulate in the phagocytes, which recognize them as foreign invaders (Rentsch et al., 1997, Br. J. Cancer 75:986-992). Liposomes have also been used to carry normal genes into a cell to treat diseases caused by defective genes (Guo et al., 2000, Biosci. Rep. 20:419-432). The versatility of liposomes, due to the variable composition, enables liposomes to be used to deliver vaccines, proteins, nucleotides, plasmids, drugs, cosmetics, or the volatile anesthetics of the invention to the body.

Liposome compositions of the invention may comprise any range of liposome and volatile anesthetic components, according to the methods and detailed description set forth herein. By way of a non-limiting example, a liposome component of a composition of the invention may include from 0.1% to 99.9% liposome component, or more preferably, from 0.1%-50% liposome component, and even more preferably, from 0.1%-30% liposome component. In various embodiments, the liposome of the invention comprises cholesterol, stearylamine, phosphatidylcholine, dioleoylphosphatidylethanolamine, or combinations thereof.

In various embodiments, the volatile anesthetics of the present invention may also be a component of a microdroplet. A micro-droplet of the invention consists of a sphere of organic liquid phase drug that ranges in diameter from about 200 Angstroms to about 10,000 Angstroms that is covered by a monolayer of a suitable lipid. Preferred lipids are phospholipids, which are natural constituents of biological membranes and as such are biologically compatible. Compounds useful for preparing microdroplets include phosphatidylcholine (lecithin), sphingomyelin, phosphatidic acid, phosphatidyl serine, phosphatidyl inositol, diphosphatidyl glycerol and phosphatidyl glycerol.

Micro-droplets may be prepared by sonication, including probe or bath sonication, homogenization, microfluidization or by high intensity mechanical agitation. The preferred method of preparing the microdroplets of the invention is by sonication with a probe sonicator. Alternatively, micro-droplets may be prepared in a bath sonicator. For small scale preparations a 1.0 cm diameter test tube is suspended, with use of a test-tube clamp, in a bath sonicator filled with water. The components of the microdroplet are first grossly mixed by shaking, Vortex mixing, Polytron or other methods. The suspension is then introduced into the bath sonicator and sonicated for 1-2 hours. If the preparation is to be done on a large scale, it is possible to omit the test tube and introduce the components of the microdroplet directly into a bath sonicator. Micro-droplets may also be produced by high intensity mechanical agitation. Useful methods include a Waring blender, a Polytron and high frequency shakers such as a commercial paint shaker. Other materials and methods useful in the preparation of microdroplets are known in the art and are described in U.S. Pat. Nos. 4,622,219, 4,725,442, and 5,091,188, Haynes et al. (1989, J. Contr. Rel. 9:1-12) and Haynes et al. (1985, Anesthesiology 63:490-499), all of which references are incorporated herein in their entirety.

Dosing

The amount of the volatile anesthetic to be administered depends on the particular indication desired. For example, the dose will depend on the type of dermatological disorder or disease intended to be treated. The dose may be different, for instance, if the delivery of the volatile anesthetic is intended to reduce a chronic dermatological disorder or disease as opposed to an acute dermatological disorder or disease. The subject's physical characteristics may also be important in determining the appropriate dosage. Characteristics such as weight, age, and the like may be important factors. For example, the volatile anesthetic may have increased potency with age, as has been demonstrated in the case of the volatile anesthetic isoflurane.

The temperature of the volatile anesthetic may also be considered as a factor in selecting an appropriate dose, as the solubility of many volatile anesthetics may be affected by the temperature of the volatile anesthetic and/or solution. For example, increases in temperature may increase the solubility, and thus potency, of the volatile aesthetic composition; this property has been demonstrated with certain volatile anesthetics. The particular dosage may also be dependent on the dosing regime chosen. For example, the volatile anesthetic composition may be delivered continuously or periodically. Conversely, the volatile anesthetic composition may be administered as a single administration as a one-time event.

Volatile anesthetics (for example, halogenated volatile anesthetic compounds) may be applied in amounts leading to concentrations in the range of about 250 to about 50,000 nanograms/cm$^2$ of target site of action, depending on the volatile anesthetic selected and the desired effect. In certain embodiments, a halogenated volatile anesthetic or volatile anesthetic may be administered to achieve a concentration of from about 5 to about 5,000,000 nanograms/cm$^2$ of target site of action. While the dose range will vary depending on the compound selected and patient variability, it is generally true that lower doses such as from about 0.01 to about 10,000 nanogram/cm$^2$ of target site of action are more suitable for treating, ameliorating or preventing a moderate dermatological disorder or disease, while higher doses such as from about 10,000 nanogram/cm$^2$ of target site of action to about 500,000 nanogram/cm$^2$ of target site of action or more are suitable for treating a severe dermatological disorder or disease. Of course, the doses may be given once (for example, for a minor single occurrence of dermatological disorder or disease), repeatedly (for example, for a moderate or chronic dermatological disorder or disease), or continuously (for example, for a severe dermatological disorder or disease). Combinations of these dosing regimes may also be used. For example, a subject suffering from a severe dermatological disorder or disease may require continuous dosing with periodic additional dosing.

In embodiments where an volatile anesthetic (for example, a volatile anesthetic, isoflurane, etc.) is mixed in a solution, such as water, saline or an artificial CSF solution, the concentration of the volatile anesthetic may vary. For example, a solution may contain volatile anesthetic in a v/v ratio of from about 1 to about 99%, from about 10 to about 75%, from about 10 to about 50%, from about 20 to about 50%, from 30 to about 50%, from about 1 to about 45%, from about 1 to about 40%, from about 1 to about 35%, from about 1 to about 30%, from about 1 to about 25%, from about 1 to about 20%, from about 1 to about 15%, from about 1 to about 10%, from about 1 to about 5%, from about 0.5 to about 5%, from about 0.1 to about 5%, from about 0.1 to about 2.5%, from about 0.5 to about 2.5%, or any range derivable therein. In these embodiments, the volatile anesthetic may be a volatile anesthetic, for example, isoflurane, and the solution may be water, a saline solution, artificial cerebrospinal fluid (ACSF), or other fluid.

The dosing and manner of delivery of the compositions of the invention may be adjusted to treat, ameliorate or prevent a dermatological disorder or disease, for example, by varying the amount, concentration, frequency of administration, and timing of administration.

The volatile anesthetic solution may also contain one or more additives, such as a surfactant, PVP, a polymer, an antimicrobial agent, a preservative etc. In certain embodiments, an volatile anesthetic composition of the present invention may comprise about: 0.1-90% of a volatile anesthetic such as isoflurane, methoxyflurane, or sevoflurane, 0.1-99% of an extractive solvent such as NMP or DMSO, 0.1-99% saline, and 0-50% other additive(s) (for example, glycerol, a surfactant, PVP, etc.). In some embodiments, it may be desirable to produce a concentrated formulation which may be subject to a final dilution prior to administration.

In various embodiments, a solution of about 10% volatile anesthetic, such as isoflurane, may be used; this solution may be administered as a one-time, continuously, and/or repeatedly to treat, ameliorate or prevent a dermatological disorder or disease. A further aspect of the compositions and methods of the invention for the treatment of a dermatological disorder or disease is the analgesic activity of the volatile anesthetics. Thus, a 10% v/v solution of a volatile anesthetic may be used to treat, ameliorate or prevent a dermatological disorder or disease. Higher concentrations and/or longer durations of volatile anesthetic may be used, in various embodiments, as necessary.

Methods of Active Agent Delivery

Volatile anesthetics of the present invention may be delivered topically. In some embodiments, specific concentrations of volatile anesthetics which may be used for topical delivery include from about 100 to about 500,000 nanogram/cm$^2$ of target site of action, from about 100 to about 250,000 nanogram/cm$^2$ of target site of action, from about 100 to about 100,000 nanogram/cm$^2$ of target site of action, from about 100 to about 50,000 nanogram/cm$^2$ of target site of action, from about 100 to about 25,000 nanogram/cm$^2$ of target site of action, or from about 100 to about 10,000 nanogram/cm$^2$ of target site of action. The specific concentration of volatile anesthetic used may vary depending on the desired effect, and in various embodiments the volatile anesthetic composition is titrated for effect: thus the concentration of volatile anesthetic used or achieved in tissues may vary depending on the specific desired result and/or the particular characteristics of the patient such as sensitivity to the volatile anesthetic.

In some embodiments, specific concentrations of volatile anesthetics which may be used to treat, ameliorate or prevent a dermatological disorder or disease include from about 100 to about 500,000 nanogram/cm$^2$ of target site of action, from about 100 to about 250,000 nanogram/cm$^2$ of target site of action, from about 100 to about 100,000 nanogram/cm$^2$ of target site of action, from about 100 to about 50,000 nanogram/cm$^2$ of target site of action, from about 100 to about 25,000 nanogram/cm$^2$ of target site of action, or from about 100 to about 10,000 nanogram/cm$^2$ of target site of action.

The pharmaceutical compositions of the invention may be dispensed to the subject under treatment with the help of an applicator. The applicator to be used may depend on the specific medical condition being treated, amount and physical status of the pharmaceutical composition, and choice of those skilled in the art.

The pharmaceutical compositions of the invention may be provided to the subject or the medical professional in charge of dispensing the composition to the subject, along with instructional material. The instructional material includes a publication, a recording, a diagram, or any other medium of expression, which may be used to communicate the usefulness of the composition and/or compound used in the practice of the invention in a kit. The instructional material of the kit may, for example, be affixed to a container that contains the compound and/or composition used in the practice of the invention or shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Other routes of administration to the affected area which are contemplated include: transdermal, mucosal, rectal, and vaginal, or topical (for example, in a carrier vehicle, a topical control release patch, in a wound dressing, a hydrocolloid, a foam, or a hydrogel, a cream, a gel, a lotion, an ointment, a liquid crystal emulsion (LCE), and/or a microemulsion). An appropriate biological carrier or pharmaceutically acceptable excipient may be used. Compounds administered may, in various embodiments, be racemic, isomerically purified, or isomerically pure.

Transmucosal Administration.

Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, a non-aerosol liquid formulation, or a dry powder, placed within or near the rectum ("transrectal" formulations), or administered to the urethra as a suppository, ointment, or the like.

Transrectal Administration.

Transrectal dosage forms may include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention may be manufactured using conventional processes. The transrectal dosage unit may be fabricated to disintegrate rapidly or over a period of several hours. The time period for complete disintegration may be in the range of from about 10 minutes to about 6 hours, e.g., less than about 3 hours.

Vaginal or Perivaginal Administration.

Vaginal or perivaginal dosage forms may include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Topical Formulations.

Topical formulations may be in any form suitable for application to the body surface, and may comprise, for example, an ointment, cream, gel, lotion, solution, paste or the like, and/or may be prepared so as to contain liposomes, micelles, and/or microspheres. In certain embodiments, topical formulations herein are ointments, creams and gels.

Transdermal Administration.

Transdermal compound administration, which is known to one skilled in the art, involves the delivery of pharmaceutical compounds via percutaneous passage of the compound into the systemic circulation of the patient. Topical administration may also involve the use of transdermal administration such as transdermal patches or iontophoresis devices. Other components may be incorporated into the transdermal patches as well. For example, compositions and/or transdermal patches may be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions may include creams, sprays, lotions, gels, ointments, eye drops, nose drops, ear drops, and the like. In such dosage forms, the compositions of the invention may be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions may contain polyethylene glycol 400. They may be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, may be impregnated with the compositions in solution, lotion, cream, ointment or other such form may also be used for topical application. The compositions may also be applied topically using a transdermal system, such as one of an acrylic-based polymer adhesive with a resinous cross-linking agent impregnated with the composition and laminated to an impermeable backing.

Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.

Additional Administration Forms.

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Application Nos. 20030147952, 20030104062, 20030104053, 20030044466, 20030039688, and 20020051820. Additional dosage forms of this invention also include dosage forms as described in PCT Application Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Solutions After a halogenated ether volatile anesthetic has been selected, it may be dissolved into a solution. The solution may be an aqueous-based solution, such as water, saline, or the like. In some variations, other fluids and solutions may be appropriate.

Various formulations of saline are known in the art and may be used with the present invention. For example, the saline may be lactated Ringer's solution, acetated Ringer's solution, phosphate buffered saline (PBS), Dulbecco's phosphate buffered saline (D-PBS), Tris-buffered saline (TBS), Hank's balanced salt solution (HBSS), or Standard saline citrate (SSC).

The saline solutions of the present invention are, in certain embodiments, "normal saline" (i.e., a solution of about 0.9% w/v of NaCl). Normal saline has a slightly higher degree of osmolality compared to blood; however, in various embodiments, the saline may be isotonic in the body of a subject such as a human patient. In certain embodiments, "half-normal saline" (i.e., about 0.45% NaCl) or "quarter-normal saline" (i.e., about 0.22% NaCl) may be used with the present invention. Optionally, about 5% dextrose or about 4.5 g/dL of glucose may be included in the saline. In various embodiments, one or more salt, buffer, amino acid and/or antimicrobial agent may be included in the saline.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents that may be included suitable for use include sterile aqueous solutions or dispersions and sterile powders for the extemporaneous preparation of sterile solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, and the like. Appropriate stabilizers or preservatives may be selected according to the route of administration desired. A particle filter or microbe filter may be used, and may be necessary according to the route of administration desired.

The weight ranges of compounds in the solution may vary. For example, in various embodiments, the composition may comprise about 1-5 wt % volatile anesthetic, about 1-5 wt % preservative/stabilizer, about 1-5 wt % NaCl, and about 85%-97% water. The ratio of volatile anesthetic to water may be varied as needed to achieve the desired treatment of dermatological disorders or diseases.

The solution and/or composition may also be sterilized prior to administration. Methods for sterilization are well known in the art and include heating, boiling, pressurizing, filtering, exposure to a sanitizing chemical (for example, chlorination followed by dechlorination or removal of chlorine from solution), aeration, autoclaving, and the like.

The active agent gas may be formulated into a solution in any number of ways. For example, it may be bubbled through the solution, for example, using a vaporizer, or it may be solubilized by agitation or by sonication. In certain embodiments, a volatile anesthetic such as a halogenated ether or a volatile anesthetic may be measured in liquid form and directly admixed into a solution. Of course, other suitable methods of dissolving the volatile anesthetic into solution may also be used. After the halogenated ether volatile anesthetic has been solubilized, it may be administered to a subject in need of treatment of a dermatological disorders or disease. In certain embodiments, a volatile anesthetic is admixed with a solution in a closed vacuum container, and the combined solutions are then mechanically agitated for 3-5 minutes and held in a thermo-neutral sonicator until use.

In certain embodiments, solutions of the present invention may be a component of an emulsion, such as a water-in-oil or an oil-in-water emulsion, including a lipid emulsion, such as a soybean oil emulsion. Certain emulsions of isoflurane have been prepared previously for intravenous (da Silva Telles, et al., 2004, Rev. Bras. Anaestesiol Campianas 54(5): 2004) or epidural administration (Chai et al. 2008, British J Anesthesia 100:109-115).

Pharmaceutical compositions of the present invention comprise an effective amount of one or more volatile anesthetics or biologically active gas or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one volatile anesthetic or biologically active gas in solution or additional active ingredient will be known to those of skill in the art in light of the present disclosure, as exemplified by "Remington: The Science and Practice of Pharmacy," 20th Edition (2000), which is incorporated herein by reference in its entirety. Moreover, for animal (for example, human) administration, it will be understood that preparations should meet sterility, pyrogenicity, general safety and purity standards as required by FDA Office of Biological Standards.

In various embodiments, the compositions of the present invention further comprise cyclodextrin. Cyclodextrins are a general class of molecules composed of glucose units connected to form a series of oligosaccharide rings (See Challa et al., 2005, AAPS PharmSciTech 6:E329-E357). In nature, the enzymatic digestion of starch by cyclodextrin glycosyl-transferase (CGTase) produces a mixture of cyclodextrins comprised of 6, 7 and 8 anhydroglucose units in the ring structure (α-, β-, and γ-cyclodextrin, respectively). Commercially, cyclodextrins are also produced from starch, but different, more specific enzymes are used. Cyclodextrins have been employed in formulations to facilitate the delivery of cisapride, chloramphenicol, dexamethasone, dextromethoraphan, diphenhydramine, hydrocortisone, itraconazole, and nitroglycerin (Welliver and McDonough, 2007, Sci World J, 7:364-371). In various embodiments, the cyclodextrin of the invention is hydroxypropyl-Beta-cyclodextrin, sulfobutylether-beta-cyclodextrin, alpha-dextrin or combinations thereof. In certain embodiments, cyclodextrin may be used as a solubilizing agent.

In various other embodiments, compositions of the present invention may comprise human serum albumin purified from plasma, or recombinant human serum albumin. In certain embodiments, human serum albumin may be used as a solubilizing agent. In other embodiments, the compositions of the invention may comprise propylene glycol. In other embodiments, the compositions of the invention may comprise perfluorooctyl bromide. In other embodiments, the compositions of the invention may comprise perfluorocarbon. In certain embodiments, perfluorocarbon may be used as a solubilizing agent.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents which may be included suitable for use include sterile aqueous solutions or dispersions and sterile powders for the extemporaneous preparation of sterile solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired. A particle filter or microbe filter may be used and may be necessary according to the route of administration desired.

Pharmaceutical Compositions and Therapies

Administration of compositions of the invention in a method of treatment may be achieved in a number of different ways, using methods known in the art. Such methods include, but are not limited to, topically administering solutions, suspensions, creams, pastes, oils, lotions, gels, foam, hydrogel, ointment, liposomes, emulsions, liquid crystal emulsions, and nanoemulsions.

The therapeutic and prophylactic methods of the invention thus encompass the use of pharmaceutical compositions of the invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. For example unit dose container may be such that volatile anesthetic solution is contained in a crushable sealed ampoule which in turn is enclosed in protective covering on which pressure is applied to crush the ampoule which then releases volatile anesthetic solution for percolation through a flint-type tip which capped the ampoule in protective covering. When such packaging configuration is employed, care is taken to leave as little as possible or ideally no headspace in ampoule for the volatile anesthetic to escape and cause a change in solution composition over a period of shelf life.

Although the description of pharmaceutical compositions provided herein are principally directed to pharmaceutical compositions which are suitable for ethical administration to humans, it will be understood by the skilled artisan that such compositions are generally suitable for administration to animals of all sorts, including mammals. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals, mammals such as non-human primates, cattle, pigs, horses, sheep, cats, and dogs.

Pharmaceutical compositions that are useful in the methods of the invention may be prepared, packaged, or sold in formulations suitable for ophthalmic, vaginal, topical, intranasal, buccal, or another route of administration.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. One non-limiting example of such an additional pharmaceutically active agent is an antimicrobial agent, such as an antibiotic.

Controlled- or sustained-release formulations of a pharmaceutical composition of the invention may be made using conventional technology.

Formulations of a pharmaceutical composition suitable for topical administration comprise the active ingredient combined with a pharmaceutically acceptable carrier, such as sterile water or sterile isotonic saline. Formulations may be prepared, packaged, or sold in unit dosage form, such as in ampules, crushable or otherwise, or in multi-dose containers containing a preservative. Formulations for topical administration include, but are not limited to, suspensions, solutions, emulsions in oily or aqueous vehicles, solutions, suspensions, creams, pastes, oils, lotions, gels, foam, hydrogel, ointment, liposomes, emulsions, liquid crystal emulsions, nanoemulsions, implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile formulations may be prepared using a non-toxic acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other formulations that are useful include those which comprise the active ingredient in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

In some embodiments, the pharmaceutical compositions of the invention may be contained in a crushable ampule irrespective of the route of delivery to the patient. Throughout this disclosure, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

It is contemplated that any embodiment discussed in this specification may be implemented with respect to any method or composition of the invention, and vice versa. Furthermore, compositions of the invention may be used to achieve methods of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Preparation of Isoflurane Dissolved in Saline

Isoflurane was dissolved into saline using the following method (also referred to as the "bubbling" method). A mock vaporizing device was created using a 500 ml modified Erlenmeyer flask (2 inlets and 1 catheter into the liquid phase). The flask was partially filled with 0.9% normal saline and a stoppered glass pipette was inserted into the bottom of the liquid phase for injection of isoflurane. A second egress pipette allowed egress of gas from the closed container. 2% isoflurane solution in oxygen at 2 L/min was injected through the pipette, saturating the 0.9% saline solution after approximately 10 minutes of bubbling.

Example 2

Isoflurane Dissolved in Artificial Cerebrospinal Fluid

Isoflurane dissolved in ACSF was prepared by the following method. Isoflurane was mixed in a closed vacuum container in a v/v ratio of 10-50% with buffered salt solution that approximates cerebrospinal fluid (pH 7.4) with the following composition (in mM): NaCl, 120; KCl, 3; $NaHCO_3$, 25; $CaCl_2$, 2.5; $MgCl_2$, 0.5; glucose, 12. The combined solutions were mechanically agitated for 3-5 minutes and then held in a thermo-neutral sonicator until use.

Example 3

Preparation of Anesthetic Compositions Comprising an Extractive Solvent

The following solutions were prepared. Isoflurane was obtained. NMP was obtained from Sigma-Aldrich Chemical company. A 40% (v/v) isoflurane-NMP solution was made adding 40 ml of isoflurane to 60 ml of NMP. A 40% (v/v) isoflurane-ethanol solution was made adding 40 ml of isoflurane to 60 ml of ethanol.

Saline compositions with varying concentrations of isoflurane and NMP were made by mixing the above NMP-isoflurane solution with saline as follows:

| Sample | Saline (ml) | Base-Isoflurane Compositions (ml) | % Isoflurane | % NMP |
|---|---|---|---|---|
| A | 0 | 10 | 40% | 60 |
| B | 2 | 8 | 32 | 48 |
| C | 4 | 6 | 24 | 36 |
| D | 5 | 5 | 20 | 30 |
| E | 6 | 4 | 16 | 24 |
| F | 8 | 2 | 8 | 12 |
| G | 10 | 0 | 0 | 0 |

Control compositions with varying concentrations of isoflurane-ethanol were made by mixing the above isoflurane-ethanol compositions with saline as follows:

| Sample | Saline (ml) | Control-Isoflurane Compositions (ml) | % Isoflurane | % Ethanol |
|---|---|---|---|---|
| H | 0 | 10 | 40% | 60 |
| I | 2 | 8 | 32 | 48 |
| J | 4 | 6 | 24 | 36 |
| K | 5 | 5 | 20 | 30 |
| L | 6 | 4 | 16 | 24 |
| N | 8 | 2 | 8 | 12 |
| M | 10 | 0 | 0 | 0 |

To determine the stability of the compositions, the following experiment may be performed. Each sample is divided into two containers containing 5 mls of the sample. One of the samples is capped. The other sample is left uncapped. Over time (1 hour, 6 hour, 24 hour, etc.), the samples are examined to see if the isoflurane has separated from solution. Furthermore, the concentration of isoflurane in each solution may be determined at each time point. The uncapped sample may be compared to the capped sample to determine the stability of the solution. Furthermore, the isoflurane-NMP compositions may then be compared to the control compositions. It is anticipated that the anesthetic compositions will remain miscible at all concentrations.

Example 4

Preparation of Anesthetic Compositions Comprising an Emulsion

Solutions of emulsified isoflurane are prepared at room temperature (20° C.) by adding liquid isoflurane to 30% Intralipid® (Sigma-Aldrich) in gas-tight glass bottles fitted with Teflon stoppers. The bottles are then vibrated on a vibrator at 50 Hz for 30 minutes. (For examples see, Zhou et al, 2006, Anesth Analg 102:129-34; Taheri et al., 1991, Anesth Analg 1991; 72:627-34).

| Sample | 30% Intralipid (ml) | Isoflurane (ml) | % Isoflurane |
|---|---|---|---|
| A | 40 | 1.28 | 3.1 |
| B | 40 | 2.55 | 6.0 |
| C | 40 | 3.48 | 8.0 |
| D | 40 | 4.45 | 10.0 |
| E | 40 | 10.0 | 20.0 |
| F | 40 | 26.67 | 40.0 |

To determine the stability of the compositions, the following experiment is performed. Each sample is divided into two containers containing 5 ml of the sample. One of the samples is capped. The other sample is left uncapped. Over time (1 hour, 6 hour, 24 hour, etc.), the samples are examined to see whether the isoflurane has separated from solution, or whether the lipid phase has separated from the aqueous phase. Furthermore, the concentration of isoflurane in each solution may be determined at each time point. The uncapped sample may be compared to the capped sample to determine the stability of the solution. It is anticipated that the anesthetic compositions will not separate at all concentrations.

One of skill in the art will realize that emulsions of isoflurane may be made using other lipids, including other emulsion preparations, such as 10% (w/v) Intralipid® or 20% (w/v) Intralipid®, using variations of the methods described herein. Other commercially available lipid compositions that may be useful for the production of the volatile anesthetic compositions of the present invention include, but are not limited to, Liposyn® (B. Braun) and Nutrilipid® (B. Braun).

One of skill in the art will also realize that emulsions of desflurane, sevoflurane, isoflurane, enflurane, methoxyflurane and halothane may be produced using variations of the methods described herein.

Example 5

Preparation of Anesthetic Compositions Comprising an Extractive Solvent and an Emulsion The following solutions and emulsions are prepared. Isoflurane is obtained. NMP is obtained from Sigma-Aldrich Chemical company. A 40% (v/v) isoflurane-NMP solution is made by adding 40 ml of isoflurane to 60 ml of NMP (as in Example 4).

Emulsion compositions with varying concentrations of isoflurane and NMP are prepared by mixing the above NMP-isoflurane solution with 30% Intralipid (Sigma-Aldrich) at room temperature (20° C.) in gas-tight bottles fitted with Teflon stoppers as follows:

| Sample | 30% Intralipid (ml) | 40% (v/v) isoflurane-NMP (ml) | % Isoflurane | % NMP |
|---|---|---|---|---|
| A | 40 | 3.37 | 3.1 | 4.7 |
| B | 40 | 7.06 | 6.0 | 9.0 |
| C | 40 | 10.0 | 8.0 | 12.0 |
| D | 40 | 13.34 | 10.0 | 15.0 |
| E | 40 | 40.0 | 20.0 | 30.0 |

After mixing, the bottles are vibrated on a vibrator at 50 Hz for 30 minutes. To determine the stability of the compositions, the following experiment is performed. Each sample is divided into two containers containing 5 ml of the sample. One of the samples is capped. The other sample is left uncapped. Over time (1 hour, 6 hour, 24 hour, etc.), the samples are examined to see whether the isoflurane has separated from solution, or whether the lipid phase has separated from the aqueous phase. Furthermore, the concentration of isoflurane in each solution is determined at each time point. The uncapped sample may be compared to the capped sample to determine the stability of the solution. It is anticipated that the anesthetic compositions will not separate at all concentrations.

One of skill in the art will realize that emulsions of isoflurane may be made using other lipids, including other emulsion preparations, such as 10% (w/v) Intralipid® or 20% (w/v) Intralipid®, using variations of the methods described herein. Other commercially available lipid compositions that may be useful for the production of the volatile anesthetic compositions of the present invention include, but are not limited to, Liposyn® (B. Braun) and Nutrilipid® (B. Braun).

One of skill in the art will also realize that emulsions of desflurane, sevoflurane, isoflurane, enflurane, methoxyflurane and halothane may be produced using variations of the methods described herein.

Example 6

Stability of Isoflurane Formulations

In the Examples that follow, the stability of isoflurane in the described compositions was determined in two ways. First, the compositions were examined for the presence of phase separation at the macroscopic level. Secondly, isoflurane content of the compositions was determined by weighing the remaining isoflurane in the composition when they were left uncapped over time. Briefly, glass vials were filled with 5-10 ml of the composition vehicle and then weighed; one of them received only vehicle (i.e., no isoflurane) and served as control. The other vials received varying amounts of isoflurane. They were left uncapped in the hood. Over time, the vials were weighed to see if the isoflurane stayed in the composition or had evaporated. The amount evaporated over time in the vehicle control was subtracted from that in the isoflurane-containing composition.

The pure form of isoflurane is a volatile anesthetic. In order to assess the volatility of isoflurane, two vials received the indicated amounts of pure form isoflurane. The vials were placed in the chemical fume hood and left uncapped. The vials were weighed at the indicated times to determine the amount of evaporated isoflurane. As it is shown in the table below 0.7893 g isoflurane was evaporated within 3 hours, while 3.4825 g isoflurane took approximately 8 hrs to evaporate completely. These amounts of isoflurane are similar to the amounts of isoflurane that were used to prepare the isoflurane compositions in the Examples that follow.

| Pure form of isoflurane (g) | 0 h (% remaining iso) | 0.25 h (% remaining iso) | 1 h (% remaining iso) | 2 h (% remaining iso) | 3 h (% remaining iso) | 5 h (% remaining iso) | 7 h | 8 h |
|---|---|---|---|---|---|---|---|---|
| 0.7893 | 100 | 85 | 52 | 14 | 0 | | | |
| 3.4825 | 100 | 96 | 86 | 75 | 62 | 38 | 13 | 3 |

Example 7

Preparation of Isoflurane Solution (v/v) with NMP

Pure isoflurane USP (Forane) liquid was mixed with NMP (Sigma-Aldrich) in the indicated concentrations; the mixture was vortexed vigorously to prepare homogenous isoflurane-NMP solution. In order to reduce the amount of NMP in the solution, saline (0.9% NaCl) was added to the mixture.

|   | NMP (%) | Saline (%) | Isoflurane (%) | Appearance of solutions |
|---|---|---|---|---|
| 1 | 90 | — | 10 | Clear |
| 2 | 60 | — | 40 | Clear |
| 3 | 63 | 27 | 10 | Clear |
| 4 | 72 | 20 | 8 | Clear |

| Isoflurane concentration in NMP | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 99 | 99 | 94 | 91 |
| 30 | 100 | 99 | 98 | 90 | 86 |

As it is shown in the tables above, 10% and 40% of isoflurane was mixed with NMP, and the resulting solution looked clear. Moreover, the addition of NMP reduced the volatility of isoflurane, as compared with Example 6.

Example 8

Preparation of Emulsified Isoflurane (v/v) in Intralipid

Pure isoflurane USP (Forane) liquid is mixed with Intralipid 20% or 30% (Baxter) at the indicated concentrations; the mixture was vortexed vigorously and sonicated for 30 minutes to prepare homogenous isoflurane-intralipid emulsion.

|   | Lipid Emulsion | Isoflurane Concentration | Appearance of Emulsions |
|---|---|---|---|
| 1 | 20% Intralipid | 1-6% | Homogenous |
| 2 | 30% intralipid | 6-10% | Homogenous |

Intralipid emulsions with the indicated amount of isoflurane looked homogenous and uniform. Moreover, intralipid reduced the volatility of isoflurane, as compared with Example 6.

One of skill in the art will realize that emulsions of isoflurane may be made using other lipids, including other emulsion preparations, such as 10% (w/v) Intralipid, using variations of the methods described herein. Other commercially available lipid compositions that may be useful for the production of the volatile anesthetic compositions of the present invention include, but are not limited to, Liposyn® (B. Braun) and Nutrilipid® (B. Braun). One of skill in the art will also realize that emulsions of desflurane, sevoflurane, isoflurane, enflurane, methoxyflurane and halothane may be produced using variations of the methods described herein.

Example 9

Preparation of Emulsified Isoflurane (v/v) in Intralipid and NMP

Pure isoflurane USP (Forane) liquid is mixed with NMP (Sigma-Aldrich) in the indicated concentrations; the NMP-Isoflurane solution was added to intralipid 20% or 30% (Baxter). The mixture was vortexed vigorously and sonicated for 30 minutes to prepare homogenous isoflurane-NMP-intralipid emulsion.

|   | 20% Intralipid (%) | NMP (%) | Isoflurane (%) | Appearance of emulsions |
|---|---|---|---|---|
| 1 | 75 | 15 | 10 | Homogenous |
| 2 | 80 | 10 | 10 | Homogenous |

| Isoflurane concentration in intralipid 20% | 0 h (% remaining iso) | 0.25 h (% remaining iso) | 1 h (% remaining iso) | 16 h (% remaining iso) | 24 h (% remaining iso) |
|---|---|---|---|---|---|
| 2 | 100 | 95 | 95 | 92 | 91.7 |
| 3 | 100 | 93 | 92 | 70 | 69.8 |
| 4 | 100 | 94 | 92 | 55 | 55.3 |
| 5 | 100 | 96 | 95 | 60 | 58.9 |

| Vehicle | Isoflurane (%) | 0 h (% remaining iso) | 0.25 h (% remaining iso) | 1 h (% remaining iso) | 16 h (% remaining iso) | 24 h (% remaining iso) |
|---|---|---|---|---|---|---|
| 20% intralipid + 15% NMP | 5 | 100 | 98 | 94 | 88 | 85 |
| 20% intralipid + 15% NMP | 10 | 100 | 98 | 97 | 93 | 89 |

Intralipid emulsions with the indicated amount of isoflurane in the presence of NMP looked homogenous and uniform. In the presence of NMP, intralipid was able to hold more isoflurane than in the absence of NMP, as compared with Example 7. In addition, the combination of intralipid and NMP reduced the volatility of isoflurane, as compared with Example 6.

One of skill in the art will realize that emulsions of isoflurane may be made using other lipids, including other emulsion preparations, such as 10% (w/v) intralipid, using variations of the methods described herein. Other commercially available lipid compositions that may be useful for the production of the volatile anesthetic compositions of the present invention include, but are not limited to, Liposyn® (B. Braun) and Nutrilipid® (B. Braun). One of skill in the art will also realize that emulsions of desflurane, sevoflurane, isoflurane, enflurane, methoxyflurane and halothane may be produced using variations of the methods described herein.

Example 10

Preparation of Polysorbate 80 (Tween 80)-Based Emulsified Isoflurane

Isoflurane was added to Tween 80 (3% v/v) for a total volume of 10 ml. The mixture was vortexed vigorously and sonicated for 30 minutes to prepare homogenous isoflurane emulsion. In some cases, 1, 2-dimyristoyl-sn-glycero-3-phophocholine (DMPC) was included in the formulation.

|   | 3% Tween 80 (%) | DMPC (%) | Isoflurane (%) | Appearance of emulsions |
|---|---|---|---|---|
| 1 | 95 | — | 5 | Homogenous |
| 2 | 93 | 0.3 | 7 | Homogenous |
| 3 | 93 | 0.6 | 7 | Homogenous |

| Vehicle | Isoflurane (%) | 0 h (% remaining iso) | 0.25 h (% remaining iso) | 1 h (% remaining iso) | 16 h (% remaining iso) | 24 h (% remaining iso) |
|---|---|---|---|---|---|---|
| 3% Tween | 7 | 100 | 97 | 95 | 91 | 85 |
| 3% Tween + 0.3% DMPC | 7 | 100 | 98 | 96 | 94 | 89 |
| 3% Tween + 0.6% DMPC | 7 | 100 | 100 | 100 | 99 | 94 |

Tween 80-based emulsions appeared homogenous. When DMPC was added, the same amount of Tween 80 was able to hold more isoflurane than without DMPC. Moreover, the combination of isoflurane with Tween 80 or Tween 80 DMPC reduced the volatility of isoflurane, as compared with Example 6.

Example 11

Preparation of Isoflurane Solution (v/v) with Propylene Glycol

Pure isoflurane USP (Forane) liquid was mixed with Propylene Glycol (Sigma-Aldrich) at the indicated concentrations; the mixture was vortexed vigorously to prepare homogenous isoflurane-Propylene Glycol solution.

|   | Propylene Glycol (%) | Saline (%) | Isoflurane (%) | Appearance of solutions |
|---|---|---|---|---|
| 1 | 90 | — | 10 | Clear |
| 2 | 70 | — | 30 | Clear |
| 3 | 72 | 20 | 8 | Clear |

First, DMPC (0.3% or 0.6%) was dissolved in Tween 80 (3% v/v), then isoflurane was added to the Tween-DMPC mixture, which was followed by 30 minutes of sonication.

| Isoflurane concentration in Propylene Glycol | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 89 | 86 | 44 | 23 |
| 30 | 100 | 94 | 90 | 53 | 35 |

Eight percent, 10% and 30% of isoflurane was mixed with propylene glycol, and the resulting solutions appeared clear. Moreover, propylene glycol reduced the volatility of isoflurane, as compared with Example 6.

Example 12

Preparation of Cremophor EL-Based Emulsified Isoflurane

Isoflurane was added to an aqueous solution of Cremophor EL (10% v/v) for a total volume of 10 ml. The mixture was vortexed vigorously and sonicated for 30 minutes to prepare homogenous isoflurane emulsion.

| | 10% Cremophor EL (%) | Isoflurane (%) | Appearance of the emulsion |
|---|---|---|---|
| 1 | 95 | 5 | Milky |
| 2 | 90 | 10 | Milky |

| Vehicle | Isoflurane Concentration | 0 h (% remaining iso) | 0.25 h (% remaining iso) | 1 h (% remaining iso) | 16 h (% remaining iso) | 24 h (% remaining iso) |
|---|---|---|---|---|---|---|
| 10% Cremophor | 5 | 100 | 90 | 85 | 68 | 54 |
| 10% Cremophor | 10 | 100 | 91 | 87 | 73 | 60 |

Cremophor EL-based emulsions with the indicated amount of isoflurane appeared milky. Moreover, the Cremophor EL-based emulsions reduced the volatility of isoflurane, as compared with Example 6.

Example 13

Preparation of Isoflurane Solution (v/v) with Dimethyl Sulfoxide (DMSO)

Pure isoflurane USP (Forane) liquid was mixed with DMSO (BDH) at the indicated concentrations. The mixture was vortexed vigorously to prepare homogenous isoflurane-DMSO solution. The isoflurane solutions containing DMSO appeared clear.

| | DMSO (%) | Saline (%) | Isoflurane (%) | Appearance of solutions |
|---|---|---|---|---|
| 1 | 90 | — | 10 | Clear |
| 2 | 50 | — | 50 | Clear |
| 3 | 72 | 20 | 8 | Clear |

Example 14

Preparation of Isoflurane Solution (v/v) in Perfluorooctyl Bromide

Pure isoflurane USP (Forane) liquid was mixed with Perfluorooctyl Bromide (Acros Organics) at the indicated concentrations. The mixture was vortexed vigorously to prepare homogenous isoflurane-Perfluorooctyl Bromide solution. The isoflurane solutions containing Perfluorooctyl Bromide appeared clear.

| | Perfluorooctyl Bromide (%) | Isoflurane (%) | Appearance of solutions |
|---|---|---|---|
| 1 | 90 | 10 | Clear |
| 2 | 80 | 20 | Clear |

Example 15

Preparation of Isoflurane Solution (v/v) in PEG 400

Isoflurane (2 mL) was mixed with PEG-400 (2 mL) in a vial and contents were shaken resulting in a clear solution. The volatility of the resulting solution was compared to the volatility of pure isoflurane using Exetech Heavy Duty Differential Pressure Manometer Model 407910. At least a 3 fold reduction of vapor pressure was observed when heated to about 39° C.

Example 16

Preparation of Isoflurane Solution (v/v) in PEG 300

Isoflurane (2 mL) was mixed with PEG-300 (2 mL) in a vial and contents were shaken resulting in a clear solution. The volatility of the resulting solution was compared to the volatility of pure isoflurane using Exetech Heavy Duty Differential Pressure Manometer Model 407910. At least a 3 fold reduction of vapor pressure was observed when heated to about 39° C.

Example 17

Preparation of Isoflurane Solution (v/v) in Diethylene Glycol Monoethyl Ether

Isoflurane (2 mL) was mixed with diethylene glycol monoethyl ether (2 mL) in a vial and contents were shaken resulting in a clear solution. The volatility of the resulting solution was compared to the volatility of pure isoflurane using Exetech Heavy Duty Differential Pressure Manometer Model 407910. At least a 3 fold reduction of vapor pressure was observed when heated to about 39° C.

The disclosures of each and every patent, patent application, and publication cited herein are hereby incorporated herein by reference in their entirety.

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a dermatological disorder or disease in a subject in need thereof,
    wherein said method comprises administering to said subject a pharmaceutically acceptable composition,
    wherein said composition comprises a pharmaceutically acceptable excipient and at least one component selected from the group consisting of:
    (a) a metered amount of a volatile anesthetic dissolved in a solution in an amount effective to treat said dermatological disorder or disease, wherein said solution further comprises at least one extractive solvent in an amount effective to reduce volatility of said volatile anesthetic, wherein said solution is a component of an emulsion;

(b) a metered amount of a liposome suspension comprising a volatile anesthetic in an amount effective to treat said dermatological disorder or disease;

(c) a metered amount of a volatile anesthetic dissolved in a solution in an amount effective to treat said dermatological disorder or disease, wherein said solution further comprises at least one extractive solvent in an amount effective to reduce volatility of said volatile anesthetic, wherein said composition further comprises a solubilizing agent;

(d) a metered amount of a micro-droplet suspension, wherein said micro-droplet suspension comprises a sphere of a volatile anesthetic in an amount effective to treat said dermatological disorder or disease, wherein said sphere is surrounded by a stabilizing layer of a phospholipid;

and any combinations thereof, wherein said volatile anesthetic is selected from the group consisting of isoflurane, halothane, enflurane, sevoflurane, desflurane, methoxyflurane, and any mixtures thereof;

wherein said dermatological disorder or disease is selected from the group consisting of itching, dry skin, sunburn, scab healing, scar growth, and any combinations thereof, whereby said dermatological disorder or disease in said subject is treated.

2. The method of claim 1, wherein said at least one extractive solvent is selected from the group consisting of dimethyl sulfoxide (DMSO), N-methyl-2-pyrrolidone (NMP), dimethylformamide, dimethylacetamide, dimethylisosorbide, ethanol, propanol, PEG-400, PEG-300, diethylene glycol monoethyl ether, isopropanol, and any combinations thereof.

3. The method of claim 1, wherein said administering is performed by a route selected from the group consisting of topical, transdermal, mucosal, rectal, vaginal, and any combinations thereof.

* * * * *